United States Patent [19]

Förtsch

[11] Patent Number: 4,777,246

[45] Date of Patent: Oct. 11, 1988

[54] 1-DIAZO-2-NAPHTHOL-4-SULFONIC ACID BY IRON-CATALYZED DIAZOTIZATION

[75] Inventor: Bruno Förtsch, Ramlinsburg, Switzerland

[73] Assignee: Ciba-Geigy Corporation, Ardsley, N.Y.

[21] Appl. No.: 841,395

[22] Filed: Mar. 19, 1986

[30] Foreign Application Priority Data

Apr. 17, 1985 [CH] Switzerland ............... 1636/85

[51] Int. Cl.$^4$ ................. C07C 113/00; C07C 113/04
[52] U.S. Cl. .................... 534/557; 534/558; 534/559; 534/562; 534/565
[58] Field of Search ............ 534/565, 558, 559, 562, 534/557

[56] References Cited

U.S. PATENT DOCUMENTS

| 2,031,180 | 9/1935 | Koch | 534/565 |
| 2,812,321 | 11/1957 | Eberhart et al. | 534/565 |

FOREIGN PATENT DOCUMENTS

| 171024 | 3/1904 | Fed. Rep. of Germany | 534/565 |
| 175593 | 10/1904 | Fed. Rep. of Germany | 534/565 |
| 178621 | 1/1905 | Fed. Rep. of Germany | 534/565 |
| 189179 | 4/1906 | Fed. Rep. of Germany | 534/565 |

OTHER PUBLICATIONS

Nesmejanow et al., Ber. Deut. Chem. Gesell., vol. 68, pp. 1877 to 1883 (1935).
Saunders, "The Aromatic Diazo-Compounds and Their Technical Applications", Edward Arnold & Co., London, pp. 7 to 9 (1936).

*Primary Examiner*—Floyd D. Higel
*Attorney, Agent, or Firm*—Kevin T. Mansfield; Edward McC. Roberts

[57] ABSTRACT

The invention relates to a process for the preparation of 1-diazo-2-naphthol-4-sulfonic acid by diazotizing 1-amino-2-naphthol-4-sulfonic acid in weakly acid medium and in the presence of iron ions, using only 1 to 30 millimoles of an iron compound per mole of 1-amino-2-naphthol-4-sulfonic acid. Such an insignificant amount is sufficient to protect the 1-amino-2-naphthol-4-sulfonic acid effectively from being oxidized to 1,2-naphthoquinonesulfonic acid and to afford the desired reaction product in good yield.

5 Claims, No Drawings

1-DIAZO-2-NAPHTHOL-4-SULFONIC ACID BY IRON-CATALYZED DIAZOTIZATION

The present invention relates to a process for the preparation of 1-diazo-2-naphthol-4-sulfonic acid by diazotising 1-amino-2-naphthol-4-sulfonic acid in weakly acid medium and in the presence of catalytic amounts of an iron salt.

1-Diazo-2-naphthol-4-sulfonic acid is an important dyestuff intermediate and is used as diazo component for synthesising a whole range of textile and leather dyes. The experiments carried out by Böniger at the turn of the century for diazotising 1-amino-2-naphthol-4-sulfonic acid did not at first lead to the desired diazo compound, but resulted in 1,2-naphthoquinone-4-sulfonic acid [Chem. Ber. 27, 3050 (1894)]. Not until it was observed that the addition of iron or copper salts inhibits the oxidation reaction to allow diazotisation to take place did 1-amino-2-naphthol-4-sulfonic acid find wide utility as diazo component in dyestuff chemistry. The precise mode of action of the metal salts during diazotisation is still today not fully understood. It is assumed, however, that co-ordinative bonding takes place between copper or iron ions and the 1-amino-2-naphthol through the hydroxyl and amino group and thus protects the hydroxyl group from oxidative attack by the nitrous acid.

As the regulations regarding wastewater pollution are becoming increasingly more stringent, every effort is being made to keep the pollution of wastewater by heavy metal salts to the minimum. In connection with the reaction described in this specification, it was already known that the desired effect, namely preventing the oxidation of the aminonaphtholsulfonic acid, is achieved with less than the equimolar amount of metal salt. It has been found that the required amount of metal salts can be still further reduced and that, surprisingly, when using iron salts, an optimum concentration range will result that is far below the stoichiometric amount required.

Accordingly, the present invention relates to a process for the preparation of 1-diazo-2-naphthol-4-sulfonic acid by diazotising 1-amino-2-naphthol-4-sulfonic acid in weakly acid medium and in the presence of iron ions, which process comprises the use of 1 to 30 millimoles of an iron compound, based on 1 mole of 1-amino-2-naphthol-4-sulfonic acid.

The 1-amino-2-naphthol-4-sulfonic acid, which can be readily obtained in good yield starting from e.g. β-naphthol via 1-nitroso-2-naphthol and 1-hydroxylimino-2-tetralone-4-sulfonic acid (q.v. Ullmanns Encyclopädie der technischen Chemie, 4th edition, Vol. 17 (1979), page 100) can be employed in the form of the free acid as well as of the alkali metal salt, e.g. the sodium or potassium salt. The starting material may be in dry form or also in the form of a filter cake that contains a larger or smaller amount of water.

The diazotisation is carried out in a weakly acid aqueous medium, by which is meant a pH value in the range from 3.5 to 6, preferably from 4 to 5. The pH is conveniently adjusted with dilute sulfuric acid.

Instead of using a mineral acid to acidify the reaction medium, it is also possible to use e.g. acetic acid or oxalic acid. To carry out the process at a preferably constant pH value, it is advisable to add a metal salt as buffer, e.g. an alkali metal salt of a weak organic acid. It is preferred to carry out the process in a solution of pH 4 to 4.5 which is acidified with sulfuric acid and buffered with acetate.

The preferred diazotisation agent is an alkali metal nitrite, e.g. sodium nitrite, which is conveniently added slowly in the form of an aqueous solution, continuously or discontinuously, to the 1-amino-2-naphthol-4-sulfonic acid suspended in the reaction medium. Further suitable diazotisation agents are the nitrites of primary and secondary aliphatic alocohols, e.g. methyl nitrite, ethyl nitrite, butyl nitrite or isopentyl nitrite. A small excess of diazotisation agent is employed, based on the stoichiometric amount required.

It is a salient feature of the invention that the diazotisation is carried out in the presence of 1 to 30 millimoles of an iron compound per mole of aminonaphtholsulfonic acid. Representative examples of iron compounds are iron salts, iron hydroxides, iron oxides or also iron complexes. Suitable salts are e.g. sulfates, nitrates, chlorides, bromides, iodides or iron carbonates. Examples of suitable oxides and hydroxides are basic iron oxide hydrates. It is preferred to use iron(II) salts, in particular iron(II) sulfate, e.g. anhydrous iron(II) sulfate or also iron(II) sulfate that contains water of crystallisation, for example iron(II) sulfate heptahydrate. The iron compounds may be in solid form as well as in dissolved form, e.g. as aqueous solution or sulfuric acid containing solution.

It is preferred to add 6 to 25 millimoles of iron compound per mole of 1-amino-2-naphthol-4-sulfonic acid. By maintaining this concentration range, the 1-diazo-2-naphthol-4-sulfonic acid is obtained in a yield of 95 to almost 100%. When using iron(II) sulfate, an optimum yield (96 to 99% of theory) is obtained if the amount of iron(II) sulfate added is 15 to 20 millimoles per mole of diazonaphtholsulfonic acid. If the amount of iron compound added is less than 1 millimole or more than 30 millimoles per mole of aminonaphtholsulfonic acid, then the yield of diazonaphtholsulfonic acid decreases appreciably. The desired diazo compound is then obtained in a yield of less than 90%.

The diazotisation is conveniently carried out in the temperature range from 0° to 60° C., with the preferred range being from 10° to 30° C. The diazotisation can also be carried out at lower temperatures, but this will result in uneconomically long reaction times.

For a 100 molar batch, the reaction time is about 20 minutes to 1 hour. The reaction course can be easily monitored from the decrease of the 1-aminonaphtholsulfonic acid suspended in the reaction medium. At the conclusion of the reaction, an aqueous solution that may still contain an insignificant amount of insoluble by-products is obtained. These impurities are conveniently removed by filtration.

The diazonaphtholsulfonic acid is precipitated in crystalline form by adding sulfuric acid to the clear reaction solution. To obtain the product in readily filterable crystalline form, it is advisable to add the amount of acid necessary to effect complete precipitation slowly over a period of several hours, while stirring the reaction mass constantly. The precipitated diazonaphtholsulfonic acid is isolated by known methods, e.g. by filtration, centrifugation or decantation. A combination of filtration and centrifugation is advantageous. The product may be processed direct with suitable coupling components to azo dyes, in particular to metallisable azo dyes for dyeing wool.

The invention is illustrated by the following Example, in which parts and percentages are by weight.

EXAMPLE

A stirred reactor is charged with 100 parts of water, in which 30 parts of 1-amino-2-naphthol-4-sulfonic acid and 7.24 parts of sodium acetate are then suspended. Then 25 parts of water are added and the pH of the suspension is adjusted to 4.2 by adding about 5 parts of 33% sulfuric acid. Then a solution of 0.62 part of iron-(II) sulfate heptahydrate ($FeSO_4.7H_2O$) in 2.3 parts of water is added (corresponding to an amount of 17.22 millimoles of iron sulfate per mole of 1-amino-2-naphthol-4-sulfonic acid). Finally, 0.073 part of an antifoam based on 2-ethyl-n-hexanol is added. The contents of the reactor are cooled to 10° C. and then, with thorough mixing, 37.5 parts of a 4N sodium nitrite solution are added. An acetylene glycol, e.g. dimethyl-4-octyne-3,6-diol, may also be used as antifoam. The temperature is kept in the range from 10° to 30° C. by cooling. To bring the diazotisation to completion, the reaction solution is stirred for 1 hour after addition of the sodium nitrite. A filter aid is then added and the reaction solution is freed from insoluble by-products by filtration. With stirring, 71.2 parts of 33% sulfuric acid are added to the clear reaction solution to precipitate the 1-diazo-2-naphthol-4-sulfonic acid in crystalline form. The product is isolated by filtration and a portion of the residual water is removed by centrifugation, affording 41.2 parts of a crude product as moist filter cake which contains 73.2% of 1-diazo-2-naphthol-4-sulfonic acid, corresponding to a yield of 96.1%.

The product is analysed by liquid chromatography. It has the same retention time as an authentic sample of 1-diazo-2-naphthol-4-sulfonic acid.

The amount of unreacted 1-amino-2-naphthol-4-sulfonic acid in the crude product is less than 0.1%. The 1-diazo-2-naphthol-4-sulfonic acid can be used direct without further purification for the synthesis of azo dyes. Comparable results are obtained by using, instead of iron(II) sulfate, an equimolar amount of iron(II) chloride or iron oxide hydrate. The same, or only a somewhat lower, yield is obtained by adding 12 or 20 millimoles, instead of 17.22 millimoles, of iron(II) salt, based on 1 mole of 1-amino-2-naphthol-4-sulfonic acid.

I claim:

1. A process for the preparation of 1-diazo-2-naphthol-4-sulfonic acid which comprises diazotising 1-amino-2-naphthol-4-sulfonic acid in an aqueous acid medium at a pH of 3.5 to 6 and in the presence of 1 to 30 millimoles of an iron compound per mole of 1-amino-2-naphthol-4-sulfonic acid.

2. A process according to claim 1, wherein the iron compound is an iron(II) salt.

3. A process according to claim 2, wherein the iron compound is iron(II) sulfate.

4. A process according to claim 1, wherein 6 to 25 millimoles of iron compound are used per mole of 1-amino-2-naphthol-4-sulfonic acid.

5. A process according to claim 3, wherein 15 to 20 millimoles of iron (II) sulfate are used per mole of 1-amino-2-naphthol-4-sulfonic acid.

* * * * *